United States Patent [19]

McLane et al.

[11] Patent Number: 5,401,733
[45] Date of Patent: Mar. 28, 1995

[54] STABLE AND ACTIVE METABOLITES OF 1,25-DIHYDROXY-16-ENE-CHOLECAL-CIFEROL

[75] Inventors: John A. McLane, West Haven, Conn.; Satyanarayama G. Reddy, c/o Women & Infants Hospital, 101 Dudley St., Providence, R.I. 02905; Milan R. Uskokovic, Upper Montclair, N.J.

[73] Assignees: Hoffmann-La Roche Inc., Nutley, N.J.; Satyanarayama G. Reddy, Providence, R.I.

[21] Appl. No.: 131,264

[22] Filed: Oct. 1, 1993

[51] Int. Cl.$^6$ ............................................. C07C 401/00
[52] U.S. Cl. ...................................... 514/167; 552/653
[58] Field of Search ......................... 552/653; 514/167

[56] References Cited

U.S. PATENT DOCUMENTS

| | | | |
|---|---|---|---|
| 4,495,181 | 1/1985 | Norman et al. | 514/167 |
| 4,501,738 | 2/1985 | Yamato et al. | 514/167 |
| 4,594,432 | 6/1986 | Baggiolini et al. | 514/167 |
| 4,612,308 | 9/1986 | Baggiolini et al. | 514/167 |
| 4,617,297 | 10/1986 | Boris et al. | 514/167 |
| 4,628,050 | 12/1986 | Maeda et al. | 514/167 |
| 4,711,881 | 12/1987 | Ikegawa | 514/167 |
| 4,719,205 | 1/1988 | DeLuca et al. | 514/167 |
| 4,804,502 | 2/1989 | Baggiolini et al. | 514/167 |
| 4,832,875 | 5/1989 | Ikekawa | 514/167 |
| 4,851,401 | 7/1989 | DeLuca et al. | 514/167 |
| 4,866,047 | 9/1989 | Yamato et al. | 514/167 |
| 4,868,165 | 9/1989 | Ikekawa | 514/165 |
| 5,001,118 | 3/1991 | Maeda et al. | 514/167 |
| 5,087,619 | 2/1992 | Baggiolini | 514/167 |
| 5,145,846 | 9/1992 | Baggiolini | 514/167 |
| 5,190,935 | 3/1993 | Bindeup et al. | 514/167 |
| 5,194,431 | 3/1993 | DeLuca et al. | 514/167 |
| 5,200,536 | 4/1993 | Ikekawa et al. | 514/167 |
| 5,260,290 | 11/1993 | DeLuca et al. | 514/167 |
| 5,292,728 | 3/1994 | Reef et al. | 514/167 |

OTHER PUBLICATIONS

Schaefer et al., "Vitamin D 1980 –eine bestandsaufnahme", Klin Woschenshcr 59:525–534 (1981).
Derwent Abstract B05 89–214489/30 E13 (1992) for EP 325 279B.
Derwent Abstract B05 90–109511/15 (1988) for EP 363 211A.
Derwent Abstract B05 82–29867E/15 (1980) for J8 7051 948B.
Derwent Abstract B5–(B1) 82–29867E/15 (1987) J8 7058352B.
Derwent Abstract B05 84–014254/03 (1982) for J8 8046728B.

*Primary Examiner*—Johann Richter
*Assistant Examiner*—Kimberly J. Kestler
*Attorney, Agent, or Firm*—George M. Gould; George W. Johnston; Robert A. Silverman

[57] ABSTRACT

The invention relates to the compounds 1,25-dihydroxy-16-ene-24-oxo-cholecalciferol and 1,24,25-trihydroxy-16-ene-cholecalciferol which stimulate differentiation of HL-60 cells, rendering them useful as an agent for the treatment of neoplastic diseases such as leukemia, and also decrease proliferation of human keratinocytes, rendering them useful as an agent for the treatment of hyperproliferative disorders of the skin such as psoriasis.

18 Claims, No Drawings

STABLE AND ACTIVE METABOLITES OF 1,25-DIHYDROXY-16-ENE-CHOLECALCIFEROL

BRIEF SUMMARY OF THE INVENTION

The invention relates to the compound 1,25-dihydroxy-16-ene-24-oxo-cholecalciferol, which can be further characterized by the formula

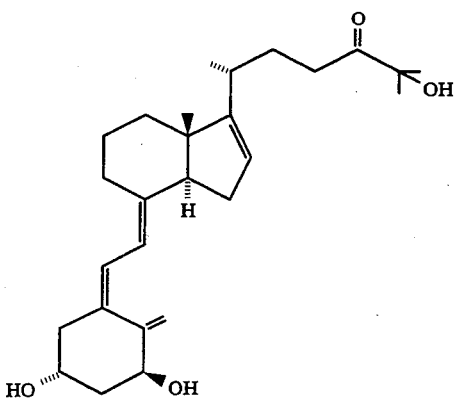

and which is useful as an agent for the treatment of neoplastic diseases, for the treatment of hyperproliferative skin diseases, and for the treatment of sebaceous gland diseases.

In another aspect, the invention relates to the compound 1,24,25-trihydroxy-16-ene-cholecalciferol, which can be further characterized by the formula

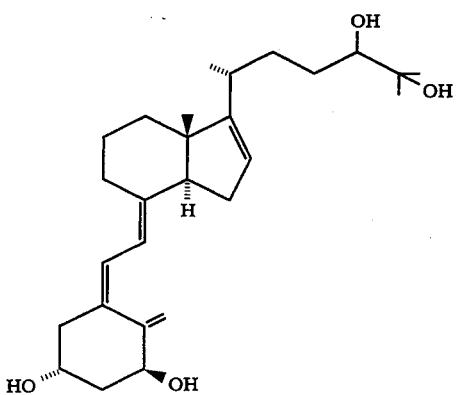

and which is useful as an agent for the treatment of neoplastic diseases, for the treatment of hyperproliferative skin diseases and for the treatment of sebaceous gland diseases.

In still another aspect, the invention relates to methods of using the compound of formulas I and II.

DETAILED DESCRIPTION OF THE INVENTION

The compounds of formulas I and II (hereinafter also 1,25(OH)$_2$-16-ene-24-oxo-D$_3$ and 1,24,25(OH)$_3$-16-ene-D$_3$, respectively) are metabolites of 1,25-dihydroxy-16-ene-cholecalciferol (hereinafter, 1,25(OH)$_2$-16-ene-D$_3$).

The compounds of formulas I and II were prepared by perfusing 1,25(OH)$_2$-16-ene-D$_3$ in rat kidneys, extracting the perfusate and isolating the compounds of formulas I and II. It was surprisingly found that 1,25(OH)$_2$-16-ene-24-oxo-D$_3$ and 1,24,25(OH)2-dihydroxy-16-ene-D$_3$ resisted further hydroxylation from other hydroxylase enzymes.

The compounds of formulas I and II stimulate differentiation of HL-60 cells which renders the compounds useful as agents for the treatment of neoplastic diseases, for example, leukemia. The compounds of formula I and II also decrease proliferation of human keratinocytes, which renders the compounds useful as agent for the treatment of hyperproliferative skin disorders, for example, psoriasis, basal cell carcinomas, disorders of keratinization, and keratosis.

The compounds of formulas I and II can be administered topically, for the treatment of hyperproliferative skin diseases such as psoriasis, basal cell carcinomas, disorders of keratinization, and keratosis, to hosts in need of such treatment such as at a dose in the range of 1 to 1000 $\mu$g per gram of topical formulation.

The compounds of formulas I and II can be administered orally, for the treatment of neoplastic diseases such as leukemia, and for the treatment of hyperproliferative skin diseases such as psoriasis, basal cell carcinomas, disorders or keratinization, and keratosis, to hosts in need of such treatment, such as at a dose in the range of 0.1 to 10 $\mu$g per day.

The activity of 1,25(OH)$_2$-24-oxo-16-ene-D$_3$ as a compound that induces differentiation of human promyelocytic cells, rendering the compound useful for the treatment of neoplastic diseases is demonstrated by the following test procedures which are known in the art.

Effect of 1,25(OH)$_2$-16-ene-24-oxo-D$_3$ on the Morphological Differentiation of HL-60 Cells

METHODS

Tissue culture medium used was RPMI-1640 (Gibco) supplemented with glutamine, antibiotics and 20% fetal bovine serum.

1,25(OH)$_2$-16-ene-D$_3$ and 1,25(OH)$_2$-16-ene-24-oxo-D$_3$ were dissolved in sufficient ethanol to yield stock solutions of 1 mM. Reduced lighting was used when working with the compounds and the stock solutions were stored in the dark at $-20$ C. in an argon atmosphere. The stock solutions were diluted in the above tissue culture medium at the concentrations indicated in Table 2 below. The stock solutions were added to flasks, which were supplemented with sufficient ethanol to achieve the final concentration of 0.1%.

A HL-60 tumor cell line was originally derived from a patient with promyelocytic leukemia and was obtained from the American Type Culture Collection (ATCC #CCL240). The cells were maintained in liquid cultures by serial passage twice weekly in the tissue culture medium. For each experimental point, cells were grown in replicate flasks. The cells were seeded at a rate of 10$^6$ cells per 25 cm$^2$ flask and grown in the presence of the compounds for a total of 4 days. Ethanol, used as the vehicle, was kept constant in all dilutions in each experiment and had no effect on the cell differentiation at the concentrations used ($>0.1\%$). After 4 days of incubation at 37° C., cultures were evaluated for cell differentiation.

Quantitation of differentiated cells was done by the biochemical method of nitroblue tetrazolium reduction (NBT) reduction. A 1 ml aliquot of cell suspension was removed from each flask and centrifuged for 10 minutes, and resuspended in about 200 $\mu$l of a work solution. The work solution contained 100 ng of tetradecanoyl phorbol acetate per ml of NBT and was kept in a covered vial on ice. The NBT was prepared fresh on the day of enumeration to 1 mg/ml in growth medium. The cells were incubated in a 37° C. water bath for 30 minutes. An aliquot was placed into a hemocytometer and the total number of blue-black cells per approximately 200 cells was determined. The percentage of differentiated cells was then calculated.

RESULTS

The results of this experiment is shown below in Table 2. The results are also shown as the concentration of compound which induced differentiation of 50% of the cells ($ED_{50}$).

TABLE 2

| Compound | Dose ($\mu M$) | Percentage of NBT postive cells | | | $ED_{50}$ ($\mu M$) |
|---|---|---|---|---|---|
| | | Exp. 1 | Exp. 2 | Average | |
| 1,25(OH)$_2$- | 0.001 | 12.0 | 18.5 | 15.25 | |
| 16-ene-D$_3$ | 0.01 | 30.5 | 47.5 | 39.0 | 0.08 |
| | 0.1 | 48.0 | 61.0 | 54.5 | |
| | 1.0 | 62.5 | 60.5 | 61.5 | |
| 1,25(OH)$_2$-16- | 0.001 | 8.0 | 24.5 | 16.25 | |
| ene-24-oxo-D$_3$ | 0.01 | 47.0 | 35.5 | 41.25 | 0.035 |
| | 0.1 | 55.0 | 60.0 | 57.5 | |
| | 1.0 | 69.0 | 70.0 | 69.5 | |
| Controls | | 1.5 | 3.25 | 2.5 | |

This data indicates that the potency of 1, 25(OH)$_2$-16-ene-24-oxo-D$_3$ is greater than that of the parent compound, 1,25(OH)$_2$-16-ene-D$_3$. Further, the effective dose necessary for inducing 50% of the cells to differentiate ($ED_{50}$) is only about 0.035 $\mu M$ for 1,25(OH)$_2$-16-ene-24-oxo-D$_3$, while it is about 0.08 $\mu M$ for the parent compound, 1, 25(OH)$_2$-16-ene-D$_3$. From the above results, it can be shown that 1,25(OH)$_2$-16-ene-24-oxo-D$_3$ induced differentiation of human promyelocytic cells.

Accordingly, 1,25(OH)$_2$-16-ene-24-oxo-D$_3$ stimulates differentiation of HL-60 cells rendering it useful as an agent for the treatment of neoplastic diseases such as leukemia.

The useful activity of 1,25(OH)$_2$-16-ene-24-oxo-D$_3$ as a compound that decreases proliferation of human keratinocytes rendering the compound useful for the treatment of hyperproliferative skin diseases can be demonstrated by the following test procedure which are known in the art.

Quantitation of Morphological Changes During Keratinocyte Proliferation Materials and Methods

1. Culture Conditions

Human neonatal foreskins were collected by circumcision and placed into tubes containing Dulbecco's Modified Eagle's Medium (DMEM) with 10% serum. On arrival at the laboratory, they were mechanically trimmed of excess dermis, and treated with a solution of trypsin/EDTA (0.05%/0.02%) at 4° C. overnight. The epidermis was stripped from the dermis, agitated in buffered saline containing soybean trypsin inhibitor to remove basal keratinocytes and the stratum cornea layer was removed. The separated cells were centrifuged, resuspended in the above media, counted, and the cells plated onto plastic culture dishes or plates at a density of 25,000 cells/cm$^2$ in keratinocyte growth media (KGM ®-modified MCDB 153, Clonetics, Inc., Catalog #CC3001) according to protocols developed by Boyce and Ham (*In Vitro Models for Cancer Research III*, 246–274, 1986) for MCDB 153 media. The cultures were incubated in humidified chambers with 5% CO$_2$ at 37° C. The cultures were refed with fresh media two to three times per week. Prior to reaching confluency the cells were replated (passage one) at 25,000 cells/well on 6-well cluster plates (Costar catalog #3506) in KGM.

2. Test Compound Solutions 1 milligram quantities were received in amber glass vials, and stored at $-20°$ C. Sufficient 100% ethanol was added directly to the vials to obtain a millimolar solution that was subsequently aliquoted into small amber vials, overlayed with argon gas and stored at 20° C. Each stock solution was thawed once, used and discarded. Aliquots from the stock solutions were diluted directly into medium and then serially diluted from micromolar to $10^{-12}$M concentrations. Dilutions from $10^{-8}$M to $10^{-12}$M had ethanol added for a final concentration of 0.1%. Stock solutions were used within one month. Control cultures were treated with 0.1% ethanol.

3. Cell Proliferation

Approximately 24 hours after passage one, the cells were refed with fresh KGM supplemented to 1.5 mM CaCl$_2$ (assay 1) containing the test compound. In a second assay (assay 2), the cells were grown in KGM without calcium supplementation to stimulate more proliferation and grown for 7 days instead of 5 days. Compounds were typically tested at 4 concentrations in triplicate wells. At the termination of the experiment, prior to the cultures reaching confluency, the cells were enumerated as follows. Dishes were rinsed with phosphate buffered saline, and then incubated with trysin/EDTA solution for 15 minutes. Cells were suspended, an aliquot placed into isotonic buffered saline and counted on an electronic particle counter (Coulter Counter). The counter was periodically calibrated for the correct size of keratinocytes. Each well was counted in triplicate. The number of cells per dish were calculated according to dilution factors used and results shown below in Table 3 are presented as percent inhibition obtained in control cultures.

TABLE 3

| Assay | Compound | Dose ($\mu M$) | Percentage Inhibition of Controls | | |
|---|---|---|---|---|---|
| | | | Exp. 1 | Exp. 2 | Average |
| 1 | 1,25(OH)$_2$-16- | 0.03 | 81.27 | 88.36 | 89.82 |
| | ene-D$_3$ | 0.1 | 81.09 | 83.56 | 82.33 |
| | | 0.3 | 78.89 | 89.05 | 84.45 |
| | | 1.0 | 58.87 | 57.11 | 58.50 |
| 2 | 1,25(OH)$_2$-16- | 0.03 | 75.58 ± 3.35 | | |
| | ene-D$_3$ | 0.1 | 56.24 ± 5.70 | | |
| | | 0.3 | 35.98 ± 10.28 | | |
| | | 1.0 | 22.35 ± 8.55 | | |
| 1 | 1,25(OH)$_2$-16- | 0.03 | 77.32 | 82.84 | 80.08 |
| | ene-24-oxo-D$_3$ | 0.1 | 70.23 | 108.04 | 89.14 |

TABLE 3-continued

| Assay | Compound | Dose (μM) | Percentage Inhibition of Controls | | |
|---|---|---|---|---|---|
| | | | Exp. 1 | Exp. 2 | Average |
| | | 0.3 | 62.31 | 73.34 | 67.82 |
| | | 1.0 | 63.13 | 73.11 | 68.12 |
| 2 | 1,25(OH)$_2$-16-ene-24-oxo-D$_3$ | 0.03 | 63.04 ± 7.21 | | |
| | | 0.1 | 45.31 ± 9.48 | | |
| | | 0.3 | 31.09 ± 11.82 | | |
| | | 1.0 | 17.40 ± 8.13 | | |
| 1 | control | | 100 ± 4.1 | 100 ± 3.87 | |
| 2 | control | | 100 ± 8.25 | | |

The data for assay 1 indicates that 1,25(OH)$_2$-16-ene-24-oxo-D$_3$ as well as 1, 25(OH)$_2$-16-ene-D$_3$ have some antiproliferative activity at lower doses, although this activity is not dose dependent. However, the data for assay 2 indicates that 1,25(OH)$_2$-16-ene-24-oxo-D$_3$ and 1,25(OH)$_2$-16-ene-D$_3$ have strong antiproliferative activity at lower doses. Further, in low calcium and more rapidly dividing cells 1,25(OH)$_2$-16-ene-24-oxo-D$_3$ and 1,25(OH)$_2$-16-ene-D$_3$ exhibited a good dose response curve. The differences between the two experiments may be due to their effect on the keratinocyte differentiation in high extracellular calcium concentrations.

These data indicate that 1,25(OH)$_2$-16-ene-24-oxo-D$_3$ restrained the proliferation of skin cells. Accordingly, 1,25(OH)$_2$-16-ene-24-oxo-D$_3$ is useful in the treatment of hyperproliferative disorders of the skin such as psoriasis.

Oral dosage forms comprising the compounds of formulas I and II may be incorporated in capsules, tablets and the like with pharmaceutically acceptable carrier materials.

Illustrative of the pharmaceutically acceptable carrier materials which may be incorporated into capsules, and the like are the following: a binder such as gum traganth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

The compounds of formulas I and II may also be administered in parenteral dosage forms, such as in the form of injection solutions and suspensions for this purpose, the compounds of formulas I and II are preferably provided as lyophilizates or dry powders for dilution with usual carriers such as water or isotonic saline.

Topical dosage forms comprising 1,25(OH)$_2$-16-ene-24-oxo-D$_3$ include: ointments and creams encompassing formulations having oleaginous, adsorbable, water-soluble and emulsion-type bases such as petrolatum, lanolin, polyethylene glycols and the like.

Lotions are liquid preparations and vary from simple solutions to aqueous or hydroalcohol preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing a compound of formulas I or II with known pharmaceutical topical carrier materials. In addition to application to the skin, the topical compositions of this invention can also be employed in the treatment of inflammations of mucous membranes, where such membranes are accesible to topical application of medication. For example, the topical composition can be applied to the mucous lining of the mouth or lower colon.

EXAMPLE 1

Preparation of compounds of formulas I and II

Crystalline 1,25(OH)$_2$-16-ene-D$_3$ was synthesized as described in U.S. Pat. No. 5,087,619, which is herein incorporated by reference to the extent necessary to enable one of skill in the art to make this invention. Rat kidneys were perfused with the 1,25(OH)$_2$-16-ene-D$_3$ as described in Am. J. Physiol. 1982, 243 E265–271 and in Biochemistry 1987, 26, 324–331. Cold 1,25(OH)$_2$-16-ene-D$_3$ (400 nmoles) was introduced into 100 mL of perfusate and the kidney perfusion was continued for 8 hours. Lipid extraction of the final kidney perfusate was performed according to the procedure described in Can. J. Biochem. Physiol. 1959, 37, 911–917. Half of the bulk lipid extract from the final perfusate of about 100 mL was then subjected directly to high pressure liquid chromatography (HPLC) performed with a Waters Model 600 equipped with a Model 990 photo diode array detector (Waters Associates, Milford, MA). HPLC analysis was performed on the lipid extract obtained from 50 mL of perfusate under the following conditions: Zorbax-SIL column (25 cm×4.6 mm); Hexane: 2-propanol (90:10), Flow rate: 2 mL/minutes. A known amount of 25(S),26(OH)$_2$-D$_3$ was added to the perfusate at the time of lipid extraction to assess extraction of vitamin D metabolites in general. Fractions of each individual metabolite from the first HPLC run was pooled and subjected to a second HPLC run using the same Zorbax-SIL column eluted with methylene chloride:2-propanol (94:5). Each metablite obtained from the second HPLC run was chromatographed twice using the first HPLC system. At this time, the purity of each metabolite was adequate for its structure identification process. A control perfusion was performed with cold 1,25(OH)$_2$-D$_3$ in a similar fashion and the lipid extract of the final perfusate was analyzed using the same HPLC systems as above.

It was found that 1,25(OH)$_2$-16-ene-D$_3$ was metabolized mainly into two metabolites. The two metabolites exhibited UV spectra with an absorbance maximum at 265 nm and an absorbance minimum at 228 nm, indicating that both the metabolites contained an intact 5,6-cis-triene chromophore. A mass spectra of 1,25(OH)$_2$-16-ene-D$_3$ and its two metabolites exhibited a peak at m/z 285, which was due to the side chain cleavage from the main steroid nucleus (C-17/C-20 cleavage). Peaks at m/z 267 and 249 were as a result of two sequential losses of water from the peak at m/z 285. A peak at m/z 152 represented the A ring plus the carbon 6 and 7 fragment. Loss of water from the peak at m/z 152 resulted in a base peak at m/z 134. Collectively the presence of common peaks at m/z 285, 267, 249, 152 and 134 in the mass spectra of 1,25(OH)$_2$-16-ene D$_3$ and its two metabolites indicated that the secosteroid nucleus remained unchanged and that the two new metabolites were formed as a result of changes occuring only in the side chain of 1,25(OH)$_2$-16-ene-D$_3$.

A molecular ion at m/z 430 (M$^+$) in the mass spectrum of one of the two metabolites suggested that this new metabolite was a trihydroxy metabolite and was formed due to addition of a hydroxy group to the side chain of 1,25(OH)$_2$-16-ene-D$_3$. A peak at m/z 59 indicated that this metabolite contained an intact C-25 hydroxy group with no hydroxylation occuring on C-26 or C-27. Also, this metabolite was susceptible to periodate oxidation and this finding suggested that the additional hydroxy group on the side chain of this new metabolite was adjacent to the C-25 hydroxy group. Thus, it was concluded that this extra hydroxy group was at C-24. This metabolite was identified as 1,24,25(OH)$_3$-16-ene-D$_3$.

A molecular ion at m/z 428 in the mass spectrum of the other metabolite suggested that this new metabolite was formed as a result of addition of an oxo functionality to the side chain of 1,25(OH)$_2$-16-ene-D$_3$. A peak at m/z 59 indicated that this metabolite, like 1,24,25(OH)$_3$-16-ene-D$_3$, contained an intact C-25 hydroxy group with no changes occuring on C-26 or C-27. This metabolite on sodium borohydride reduction was converted into a product which comigrated with 1,24,25(OH)$_3$-16-ene-D$_3$ on HPLC. This metabolite was identified as 1,25(OH)$_2$-16-ene-24-oxo-D$_3$.

| Oral Dosage Form Soft Gelatin Capsule | |
|---|---|
| | mg/capsule |
| 1,25(OH)$_2$-16-ene-24-oxo-D$_3$ | 0.0001–0.010 |
| Butylated Hydroxytoluene (BHT) | 0.016 |
| Butylated Hydroxyanisole (BHA) | 0.016 |
| Compound B | 160 |
| Myglyol ®-812 qs | |

1. Suspend BHT and BHA in Myglyol ®-812. Warm to about 50° C., and stir until dissolved.
1. Dissolve 1,25(OH)$_2$-16-ene-24-oxo-D$_3$ in the solution from Step 1.
3. Fill the solution from Step 2 in a soft gelatin cap.

All steps are performed under a nitrogen atmosphere and protected from light.

EXAMPLE 3

| Oral Dosage form Soft Gelatin Capsule | |
|---|---|
| | mg/capsule |
| 1,24,25(OH)$_3$-16-ene-D$_3$ | 0.0001–0.010 |
| BHT | 0.016 |
| BHA | 0.016 |
| Polyethylene Glycol 400 qs | 160 |

1. Suspend BHT and BHA in Polyethylene Glycol 400. Warm to about 50° C., and stir until dissolved.
2. Dissolve 1,24,25(OH)$_3$-16-ene-D$_3$ in the solution from Step 1.
3. Fill the solution from Step 2 in a soft gelatin cap.

All steps are performed under a nitrogen atmosphere and protected from light.

EXAMPLE 4

| Oral Dosage form Soft Gelatin Capsule | |
|---|---|
| | mg/capsule |
| 1,25-(OH)$_2$-16-ene-24-oxo-D$_3$ | 0.001–0.010 |
| α-Tocopherol | 0.016 |
| Myglyol ®-812 qs | 160 |

1. Suspend α-Tocopherol in Myglyol ®-812. Warm to about 50° C., and stir until dissolved.
2. Dissolve 1,25-(OH)$_2$-16-ene-24-oxo-D$_3$ in the solution from Step 1.
3. Fill the solution from Step 2 in a soft gelatin cap.

All steps are performed under a nitrogen atmosphere and protected from light.

EXAMPLE 5

| Oral Dosage form Soft Gelatin Capsule | |
|---|---|
| | mg/capsule |
| 1,24,25(OH)$_3$-16-ene-D$_3$ | 0.0001–0.010 |
| α-Tocopherol | 0.016 |
| Polyethylene Glycol 400 qs | 160 |

1. Suspend α-Tocopherol in Polyethylene Glycol 400. Warm to about 50° C., and stir until dissolved.
2. Dissolve 1,24,25(OH)$_3$-16-ene-D$_3$ in the solution from Step 1.
3. Fill the solution from Step 2 in a soft gelatin cap.

All steps are performed under a nitrogen atmosphere and protected from light.

It is claimed:
1. 1,25-dihydroxy-16-ene-24-oxo-cholecal-ciferol.
2. A pharmaceutical composition comprising an effective amount of 1,25-dihydroxy-16-ene-24-oxo-cholecalciferol and a carrier material.
3. A topical pharmaceutical composition in accordance with claim 2, wherein the amount of 1,25-dihydroxy-16-ene-24-oxo-cholecalciferol is from about 1 to 1000 μg.
4. An oral pharmaceutical composition in accordance with claim 2, wherein the amount of 1,25-dihydroxy-16-ene-24-oxo-cholecalciferol is from about 0.1 to 10 μg.
5. A method for stimulating differentiation of HL-60 cells which comprises administering to a host in need of such treatment an effective amount of 1,25-dihydroxy-16-ene-24-oxo-cholecalciferol.

6. A method of claim 5, wherein 1,25-dihydroxy-16-ene-24-oxo-cholecalciferol is administered orally in an amount of from about 0.1 to 10 μg per day.

7. A method for decreasing proliferation of human keratinocytes which comprises administering to a host in need of such treatment an effective amount of 1,25-dihydroxy-16-ene-24-oxo-cholecalciferol.

8. A method of claim 7, wherein 1,25-dihydroxy-16-ene-24-oxo-cholecalciferol is administered orally in an amount of from about 0.1 to 10 μg per day.

9. A method of claim 7, wherein 1,25-dihydroxy-16-ene-24-oxo-cholecalciferol is administered topically in an amount of from about 1 to 1000 μg per gram of topical formulation per day.

10. 1,24,25-trihydroxy-16-ene-cholecalciferol.

11. A pharmaceutical composition comprising an effective amount of 1,24,25-trihydroxy-16-ene-cholecalciferol and a carrier material.

12. A topical pharmaceutical composition in accordance with claim 11, wherein the amount of 1,24,25-trihydroxy-16-ene-cholecalciferol is from about 1 to 1000 μg.

13. An oral pharmaceutical composition in accordance with claim 11, wherein the amount of 1,24,25-trihydroxy-16-ene-cholecalciferol is from about 1 to 10 μg.

14. A method for stimulating differentiation of HL-60 cells which comprises administering to a host in need of such treatment an effective amount of 1,24,25-trihydroxy-16-ene-cholecalciferol.

15. A method of claim 14, wherein 1,24,25-trihydroxy-16-ene-cholecalciferol is administered orally in an amount of from about 0.1 to 10 μg per day.

16. A method for decreasing proliferation of human keratinocytes which comprises administering to a host in need of such treatment an effective amount of 1,24,25-trihydroxy-16-ene-cholecalciferol.

17. A method of claim 16, wherein 1,24,25-trihydroxy-16-ene-cholecalciferol is administered orally in an amount of from about 0.1 to 10 μg per day.

18. A method of claim 16, wherein 1,24,25-trihydroxy-16-ene-cholecalciferol is administered topically in an amount of from about 1 to 1000 μg per gram of topical formulation per day.

* * * * *